(12) United States Patent
Mizutani et al.

(10) Patent No.: US 6,550,957 B2
(45) Date of Patent: Apr. 22, 2003

(54) DEVICE AND METHOD FOR PREPARING CALCIUM PHOSPHATE-BASED CEMENT

(75) Inventors: Yoichiro Mizutani, Aichi (JP); Takenori Sawamura, Aichi (JP); Masateru Hattori, Aichi (JP); Masahiko Okuyama, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/079,568

(22) Filed: Feb. 22, 2002

(65) Prior Publication Data

US 2002/0118596 A1 Aug. 29, 2002

Related U.S. Application Data

(63) Continuation of application No. 09/595,903, filed on Jun. 20, 2000, now Pat. No. 6,367,962.

(30) Foreign Application Priority Data

Oct. 7, 1999 (JP) .......................................... 11-287302

(51) Int. Cl.[7] .......................... A61C 5/06; A61M 37/00; B01F 15/02; B01F 11/01
(52) U.S. Cl. ........................ 366/189; 366/195; 366/247; 433/90; 604/82; 606/93; 222/235; 222/260; 222/390
(58) Field of Search .............................. 366/189, 194, 366/195, 196, 139, 289, 267, 255, 256, 247, 258, 130; 604/218, 82; 606/93; 222/235, 260, 390

(56) References Cited

U.S. PATENT DOCUMENTS

| | | |
|---|---|---|
| 2,825,134 A | 3/1958 | Hicks |
| 3,140,078 A | 7/1964 | Krahe et al. |
| 3,188,057 A | 6/1965 | Trumbull |
| 3,417,971 A | 12/1968 | Blank et al. |
| 3,475,010 A | 10/1969 | Cook et al. |
| 3,724,077 A | 4/1973 | Preston et al. |
| 3,752,364 A | 8/1973 | DeVries |
| 3,858,853 A | 1/1975 | Rausch et al. |
| 4,371,094 A | 2/1983 | Hutter, III |
| 4,469,153 A | 9/1984 | Morrisette |
| 4,526,295 A | 7/1985 | Morel et al. |
| 4,676,655 A | 6/1987 | Handler |
| 4,799,801 A | 1/1989 | Brüning |
| 4,863,072 A | 9/1989 | Perler |
| 4,952,065 A | 8/1990 | Kreuziger |
| 4,966,468 A | 10/1990 | Brüning |
| 5,071,040 A | 12/1991 | Laptewicz, Jr. |
| 5,842,786 A | 12/1998 | Solomon |
| 6,149,655 A | 11/2000 | Constantz et al. |

FOREIGN PATENT DOCUMENTS

| | | |
|---|---|---|
| DE | 3640279 A1 | 6/1987 |
| DE | 195 32 015 A1 | 3/1997 |
| EP | 0 445 951 A1 | 9/1991 |
| EP | 0 603 871 A1 | 6/1994 |
| EP | 0 692 229 A1 | 1/1996 |
| GB | 2 338 428 | 12/1999 |
| JP | 5-317334 | 12/1993 |
| JP | 9-327468 | 12/1997 |
| JP | 10-314181 | 12/1998 |
| WO | WO 86/06618 | 11/1986 |
| WO | WO 90/13264 | 11/1990 |
| WO | WO 97/21485 | 6/1997 |

*Primary Examiner*—Tony G Soohoo
(74) *Attorney, Agent, or Firm*—Sughrue Mion, PLLC (57) ABSTRACT

A kneading device adapted for preparing calcium phosphate-based cement and for applying the cement directly to a required site which comprises a cylinder 1 which includes a hollow cylindrical body portion 11 and a nozzle 12 formed at the distal end of the cylindrical body portion; a plug 2 having an axial through-hole 21 slidably disposed within the proximal end of the cylindrical body portion; a piston assembly 3 which includes a shaft 31 extending through the through-hole 21 of the plug 2 for axial and rotatable movement, a kneading element 32 at the distal end of the shaft 31 within the cylindrical body portion, and a handle 34 formed at the proximal end of the shaft 31 external of the cylindrical body portion; a cover member 4 attached to and forming a closure for the nozzle 12; and a stop member 5 for locating the plug 2 in position at the proximal end of the cylindrical body portion.

7 Claims, 9 Drawing Sheets

DEVICE AND METHOD FOR PREPARING CALCIUM PHOSPHATE-BASED CEMENT

This is a continuation of application Ser. No. 09/595,903 filed Jun. 20, 2000 now U.S. Pat. No. 6,367,962; the disclosure of which is incorporated herein by reference.

FIELD OF THE INVENTION

This invention relates to a device suitable for preparing by kneading a calcium phosphate-based cement which may be utilized as a dental or medical cement and for applying the resultant kneaded cement to a treatment site, and to a method for preparing a calcium phosphate-based cement. More particularly, the invention relates to a kneading device for preparing calcium phosphate-based cement and for applying the resultant kneaded cement to defective portions of bone, for example bone which has suffered fracture or osteoporosis, or applying the resultant kneaded cement as an adhesive for bonding artificial bone, such as that formed from metal or ceramic, to bone, as well as to a method for preparing the calcium phosphate-based cement.

BACKGROUND OF THE INVENTION

Calcium phosphate-based cement, which contains a predominant amount of calcium phosphate, is identical to the inorganic component of bones or teeth. Calcium phosphate-based cement therefore exhibits high bio-compatibility and is useful in certain fields of medical treatment, such as orthopedics and anaplasty. Such calcium phosphate-based cement is conventionally prepared by mixing calcium phosphate powder and a kneading liquid, such as distilled water, for example, in a mortar to obtain kneaded cement which may then be filled into or applied to a defective portion of bone or tooth using a syringe or spatula and then allowed to cure.

However, the whole procedure involves strenuous labor in kneading whether performed manually or with motor assistance and in introducing the kneaded cement into a syringe. Further, foreign matter or unwanted bacteria may enter the cement during the course of kneading or of introduction into the syringe.

An object of the present invention is to solve the above problems encountered in the conventional procedure and to provide a kneading device for calcium phosphate-based cement which facilitates kneading and is capable of preventing entry of foreign matter or unwanted bacteria into the cement being kneaded, as well as to provide a method for preparing and applying calcium phosphate-based cement.

SUMMARY OF THE INVENTION

The kneading device according to the invention suitable for preparing calcium phosphate-based cement comprises: a cylinder, which includes a hollow cylindrical body portion and a nozzle formed at the distal end of the cylindrical body portion; a plug including an axial through-hole slidably disposed within the cylindrical body portion; a piston assembly which includes a shaft extending through the through-hole of the plug for axial and rotatable movement, a kneading element at the distal end of the shaft within the cylindrical body portion and a handle formed at the proximal end of the shaft external of the cylindrical body portion; a cover member attached to and forming a closure for the nozzle; and a stop member for locating the plug in position at the proximal end of the cylindrical body portion.

The method according to the present invention for preparing calcium phosphate-based cement comprises the steps of: introducing calcium phosphate-based cement and a kneading liquid into the hollow interior space defined by the cylinder and the plug of the kneading device described above; subjecting the piston to axial and rotary movement relative to the cylinder thereby to knead the calcium phosphate-based cement and the kneading liquid into kneaded cement; retracting the piston assembly such that the kneading element contacts the plug; detaching the cover member and the stop member; and moving the piston assembly towards the nozzle so as to extrude the kneaded cement from the cylinder through the nozzle.

BRIEF DESCRIPTION OF THE DRAWINGS

FIGS. 9(a) and (b), 10(a) and (b), 11(a) and (b) and 12(a) and (b) are respectively side and sectional views of different forms of kneading elements; and FIGS. 13(a) and (b) are side sectional views of still further forms of device according to the invention.

DETAILED DESCRIPTION OF THE INVENTION

The kneading device of the invention may be formed or manufactured from resin, metal or hard rubber, but is preferably of a synthetic resin, such as polypropylene, polyethylene, polystyrene, polycarbonate, polyamide, polyacetal or polyester.

The cylinder preferably assumes a right cylindrical form. The amount of cement that can be kneaded within the cylinder is preferably equal to or slightly greater than the amount of cement to be consumed in a single phase of treatment (for example, when the amount of cement to be consumed in a single treatment is 10 ml, the capacity of the cylinder may be 10–13 ml). If the capacity of the cylinder is less than the amount of cement to be consumed in a single phase of treatment, kneading must be performed several times. Alternatively, if the capacity of the cylinder is greatly in excess of the amount of cement to be consumed in a single phase of treatment, wastage of kneaded cement will result.

The plug may assume any form so long as it is slidable within the cylinder body and does not permit escape of kneaded cement from the cylinder, and preferably assumes a substantially cylindrical form corresponding to the interior profile of the cylinder body. An O-ring may be fitted into a groove formed on at least either an inner wall surface or an outer wall surface of the plug. The O-ring fitted to a sliding portion of the plug prevents escape of the kneaded cement from the device and entry of unwanted bacteria into the device, and facilitates sliding of the plug and rotation of the shaft.

Means for allowing the shaft of the piston assembly to move vertically (axially) and to rotate may assume any form. Examples of such means include screw cam mechanisms formed on the shaft and a through-hole formed in the plug and extending along the center axis of the plug. Preferably, a screw mechanism is employed. By employing such a screw mechanism, the kneading element formed on the distal end of the shaft can be moved vertically when the shaft is rotated. Further, the plug can be moved vertically when the shaft portion is moved vertically without being rotated.

Figure 3:
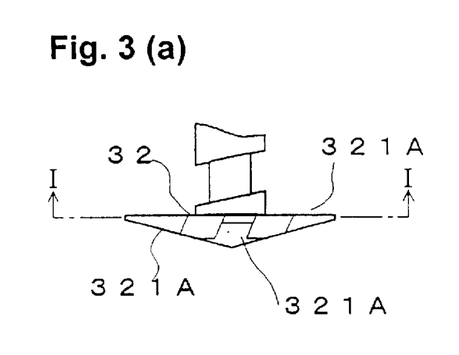
FIG. 3(a) is a side view of the stirring blades of the device of FIGS. 1 and 2.
FIG. 3(b) is a sectional view taken along line I—I of FIG. 3(a)

The kneading element may assume any form so long as it can homogeneously knead cement and a kneading liquid. The kneading element may incorporate one or more stirring blades arranged circumferentially along its side edges. The stirring blade may assume any form so long as it exhibits good stirring performance. Examples of such forms of stirring blades include those represented by blades 321A, 321B, 321C, 321D, and 321E shown in FIGS. 3 and 9–12, described in detail below. The form represented by the stirring blade 321A of FIG. 3 is particularly preferred. The stirring blade 321A further improves stirring performance. The shaft having such a stirring blade 321A is preferably threaded at a pitch of 5–25 mm (more preferably 6–20 mm, most preferably 7–15 mm). By using such a threaded shaft and stirring blade, homogeneously kneaded cement can be easily prepared within a short period of time.

The handle may assume any form so long as (1) it enables the piston assembly to be rotated for kneading, and (2) it enables the piston assembly and the plug to move towards the nozzle so as to extrude kneaded cement from the cylinder through the nozzle. Examples of such a form of the handle include a bar, a Y shape, a cross, a disk, or a polygonal plate. In order to facilitate rotation, a knob may be attached eccentrically to the handle.

The nozzle may assume any form so long as it allows introduction into the cylinder of calcium-phosphate-based cement and a kneading liquid and ejection of kneaded cement to the exterior of the cylinder. Examples of the nozzle include a Luer-Lok form, which is employed in commercially available syringes. Employment of a Luer-Lok form enables easy attachment to and detachment from the nozzle of an injection needle or a catheter for use with such a commercially available syringe.

The cover member may assume any form so long as it prevents unwanted escape of kneaded cement from the cylinder through the nozzle. Examples of such a cover include a closed-bottomed form for covering the nozzle, a pin-like form for insertion into the nozzle and an appendix form that forms with the nozzle a one-piece unitary element and is broken off for opening the nozzle.

Figure 13:
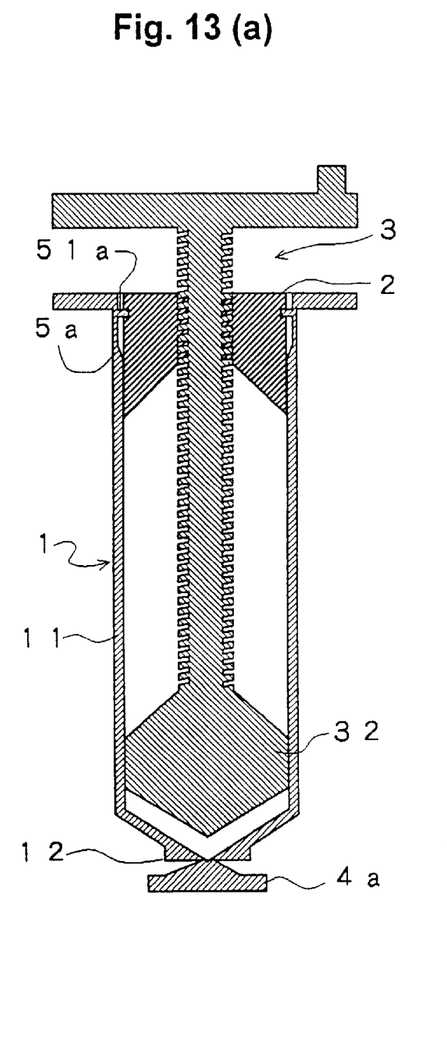

The stop member may assume any form so long as it can fix the plug within the cylinder at a predetermined position while the kneading element is performing its kneading function. Examples of such a stop member include a pin to be inserted for fixation or a screw to be screwed for fixation (FIG. 2, for example) or an elastic element that forms with the plug or the cylinder a one-piece unitary form and is snap-engaged with the cylinder or the plug (FIG. 13, for example).

Specific embodiments of the device of the invention will now be described with reference to the accompanying drawings.

Figure 1:
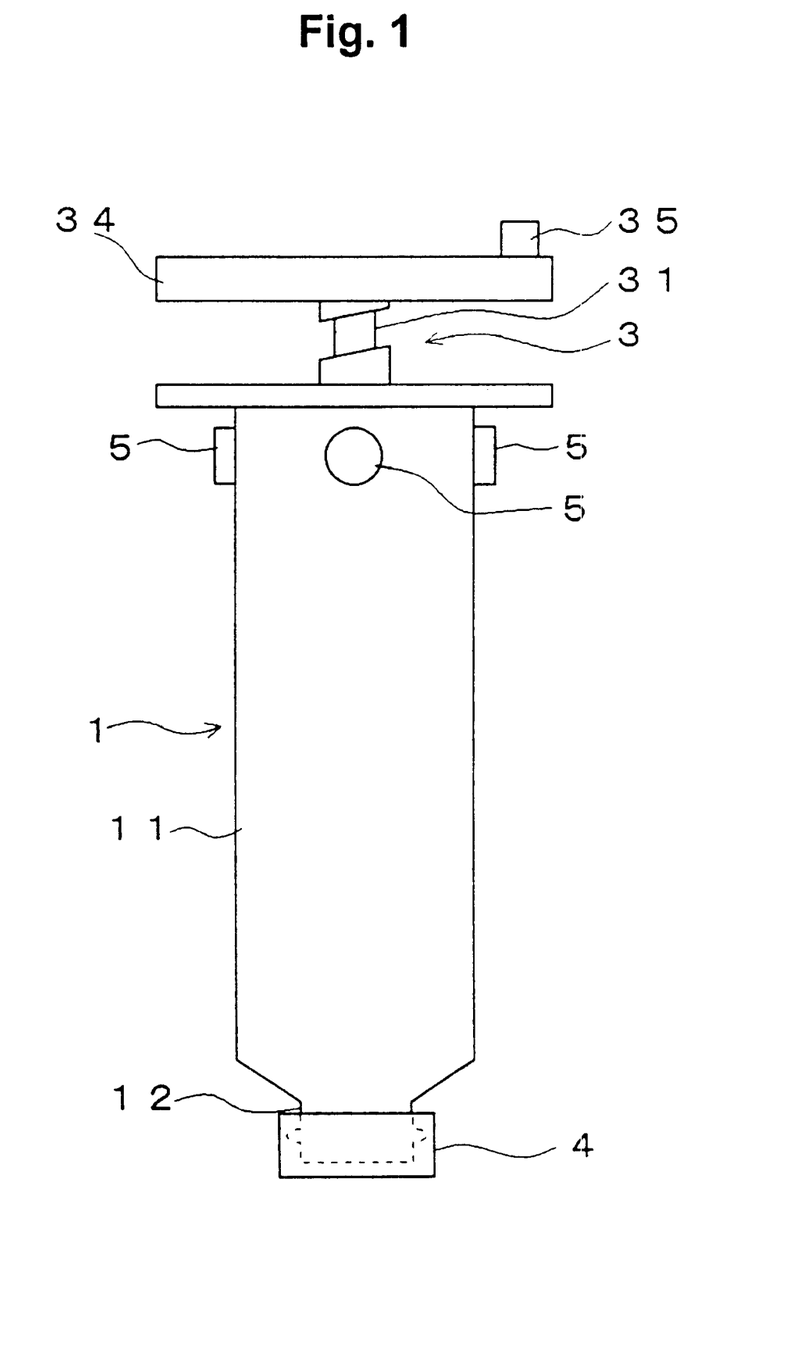
FIG. 1 is a side view of a kneading device according to the invention.
Figure 2:
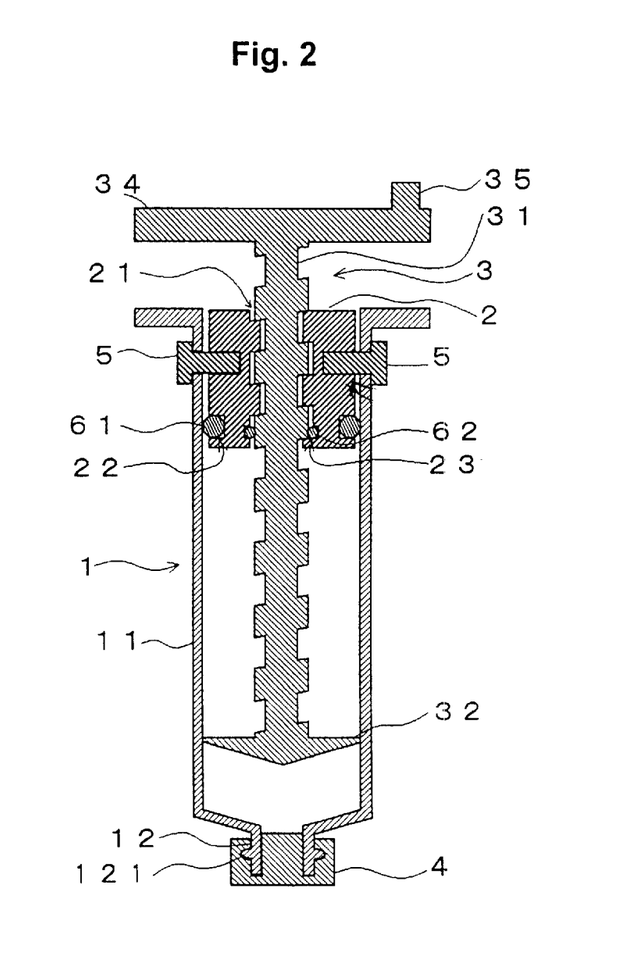
FIG. 2 is a side sectional view of the device of FIG. 1.

A kneading device suitable for calcium phosphate-based cement shown in FIGS. 1 and 2 is formed from polypropylene and includes a cylinder 1, a plug 2, a piston assembly 3, a cover member 4, and stop members 5.

The cylinder 1 has a length of about 100 mm and a diameter of about 25 mm and includes a hollow cylindrical body portion 11 of substantially right cylindrical shape and a nozzle 12 formed at one end of the cylindrical body portion 11 and adapted for the extrusion of kneaded cement therethrough. The cylinder 1 can be used to prepare approximately 10 ml of kneaded cement in a single operation. The nozzle 12 includes a protrusion 121 which constitutes a Luer-Lok structure.

As shown in FIG. 2, the plug 2 assumes a substantially cylindrical form. It is inserted into the cylinder 1 through the top open end of the cylinder 1 and is fixed in place by means of the stop members 5. An internally-threaded through-hole 21 is formed axially in the plug 2. Reception holes for the stop members 5 are formed in the side wall of the plug 2. Circumferential grooves 22 and 23 are formed in the side wall and the internally-threaded through-hole 21, respectively, of the plug 2, and O-rings 61 and 62 formed of silicone resin are fitted into the grooves 22 and 23, respectively.

As shown in FIGS. 2 and 3, the piston assembly 3 includes a shaft 31, a kneading element 32, four stirring blades 321A and a handle 34 including a knob 35. The shaft 31 assumes the form of an externally-threaded rod. The external threads of the shaft 31 engage the internal threads 21 of the plug 2, whereby rotation of the shaft 31 causes the piston assembly 3 to move vertically (axially) within the cylinder 1.

As shown in FIG. 3(*a*), the kneading element 32 is located at a distal end of the shaft 31. As shown in FIGS. 3(*a*) and 3(*b*), the kneading element 32 includes four stirring blades 321A, which extend radially from the center of the kneading element 32. Each stirring blade 321A has a substantially wedge-like section; i.e., the thickness of the blade decreases towards its radially outer end.

As shown in FIGS. 1 and 2, the handle 34 assumes the form of a disk, the center of which is attached to the proximal end of the shaft 31. The handle 34 has an eccentric knob 35 formed on its upper side which serves for rotating the shaft 31. The handle 34 also serves as a finger rest for moving the piston assembly 3 and the plug 2 toward the nozzle 12 so as to extrude kneaded cement from the cylinder 1.

The cover member 4 is engaged with the protrusion 121 of the nozzle 12 of the cylinder 1 and is adapted to prevent escape of cement from the cylinder 1 while the cement is being kneaded. The cover 4 has a protrusion formed at its center so as to prevent kneaded cement from remaining within the cover 4.

Each of the stop members 5 assumes the form of a pin for fixing the plug 2 in place within the cylinder 1. Each stop member 5 is inserted through a corresponding through-hole formed in the side wall of the cylinder 1 and into a corresponding reception hole formed in the side wall of the plug 2, thereby fixing the plug 2 within the cylinder 1 at a predetermined position.

The kneading device described above can be easily manufactured and can be stored in a sterile state before use. The kneading device may be used as a disposable tool.

A method for kneading calcium phosphate-based cement by using the kneading device described above will now be described.

Figure 5:
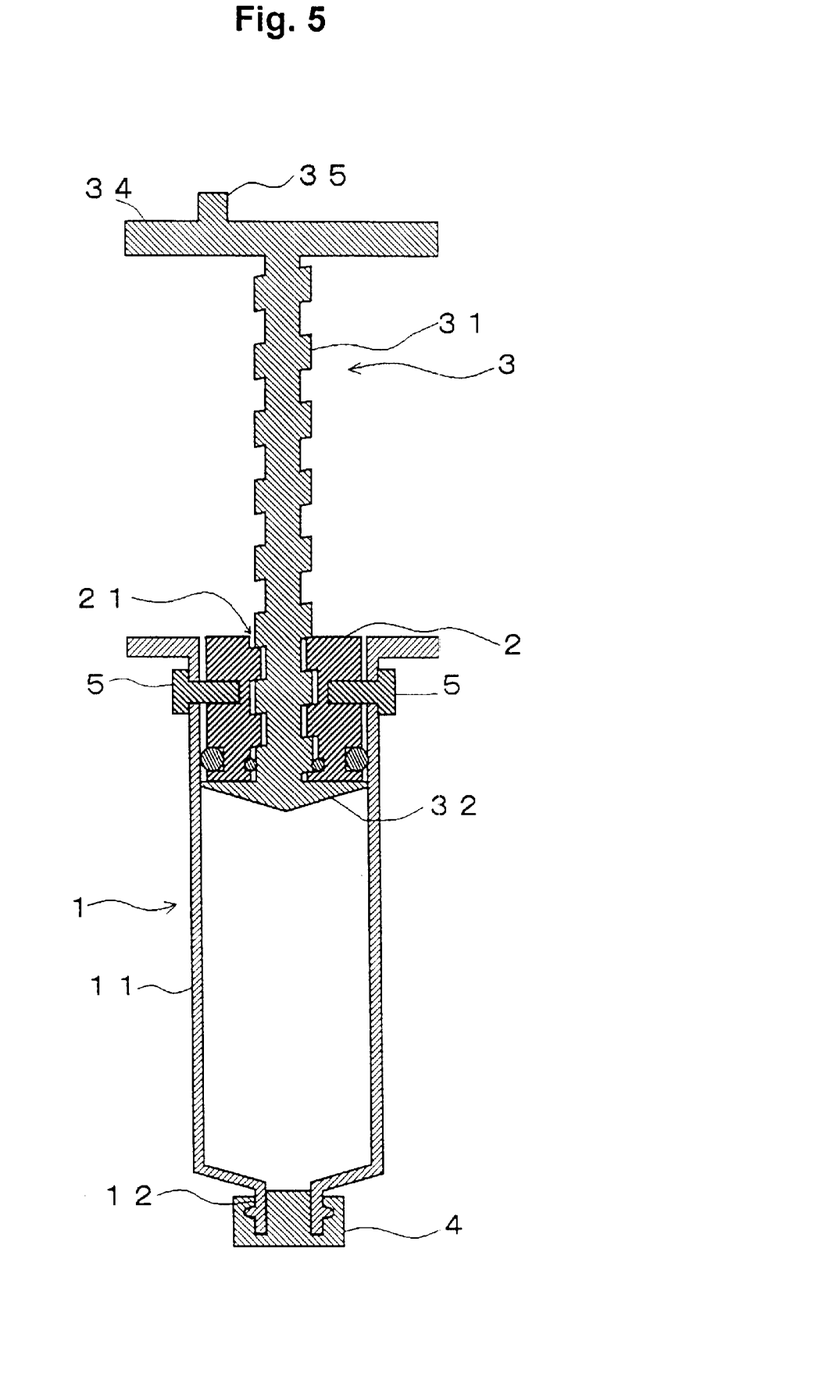
FIG. 5 is a side sectional view of the kneading device of FIG. 1 with the kneading element fully retracted.

In order to prevent escape of cement through the nozzle 12 in the course of kneading, the cover member 4 is attached to the nozzle 12 to thereby block the nozzle. A predetermined amount of cement is then placed into the cylinder 1. The plug 2 is inserted into the cylinder and is fixed in place by means of the stop members 5. As shown in FIG. 5, the plug 2 and the piston assembly 3 are engaged beforehand, the shaft 31 of the piston assembly 3 being screw-engaged with the internally-threaded through-hole 21 of the plug 2, and the kneading element 32 being in with the plug 2.

Subsequently, the device containing cement is irradiated with γ rays for sterilization. Since the subsequent kneading operation is performed within the closed device, entry of foreign matter or unwanted bacteria into the device can be prevented.

The cover member 4 is thereafter removed from the nozzle 12. A Luer-Lok syringe containing a kneading liquid is then connected to the nozzle 12 via a Luer-Lok (not shown) and kneading liquid is injected into the device from the syringe. Subsequently, the syringe is disconnected from the device and the cover member 4 is re-attached to the nozzle 12 to thereby block the nozzle.

Figure 4:
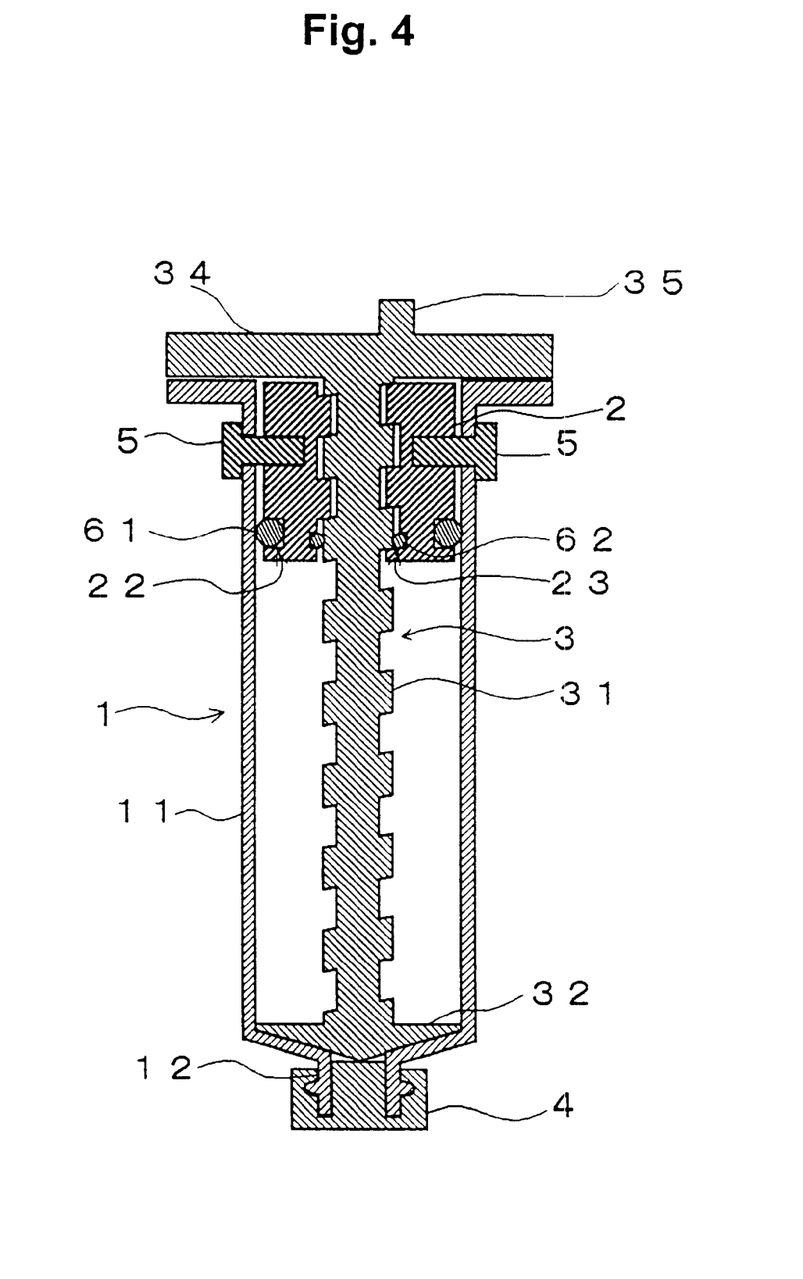
FIG. 4 is a side sectional view of the kneading device of FIG. 1 with the kneading element fully advanced.

The kneading device is gently shaken for perhaps 10–15 seconds. Then, the handle 34 is rotated while the knob 35 is grasped in the operator's fingers, so as to move the kneading element 32 axially towards the nozzle 12 as shown in FIG. 4. Subsequently, the handle 34 is rotated counterclockwise so as to move the kneading element 32 axially towards the plug 2 as shown in FIG. 5. This back-and-forth operation is repeated, for example, 3–10 times to thereby knead the cement and the kneading liquid.

Figure 6:
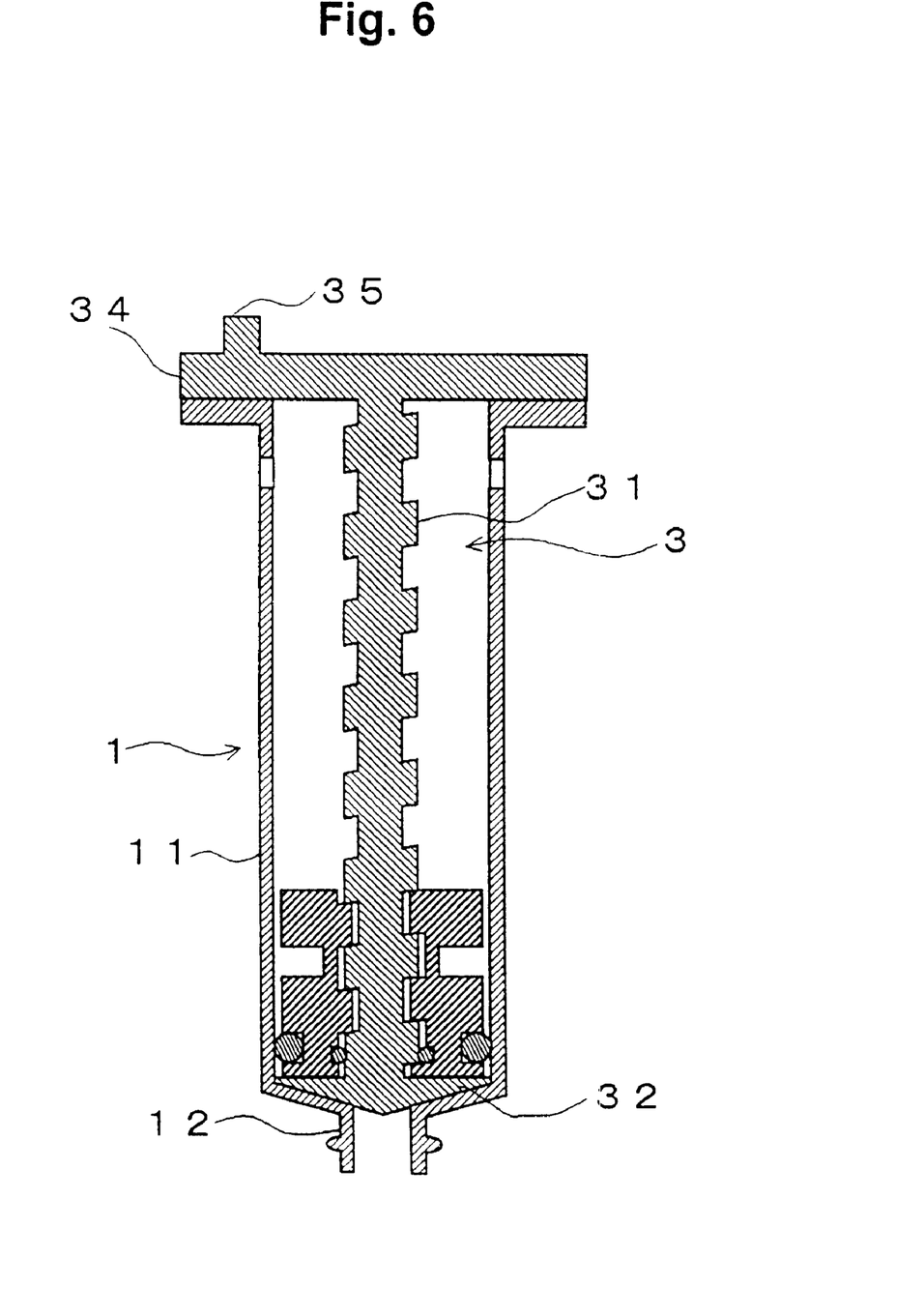
FIG. 6 is a side sectional view of the kneading device of FIG. 1 with the kneading element and plug fully advanced.

The cover member 4 and the stop members 5 are then removed from the cylinder 1. Subsequently, as shown in FIG. 6, the handle 34 is pressed down so as to move the piston assembly 3 together with the plug 2 axially towards the nozzle 12, thereby extruding kneaded cement from the cylinder 1 through the nozzle. The extruded cement is filled into or applied to a target site, such as a defective portion of bone.

When the pasty kneaded cement is of low viscosity, the cement may be filled into or applied to a target site through a Luer-Lok catheter or a Luer-Lok injection needle attached to the nozzle 12.

As described above, rotation of the handle 34 causes rotation of the threaded shaft 31. As a result, the stirring blades 321A formed on the kneading element 31 located at the distal end of the shaft 31 rotate and move vertically while stirring the cement and the kneading liquid contained in the cylinder 1. Thus, this kneading operation requires less force and consumes less time than does kneading by use of a mortar.

Further, kneading is performed within a closed space defined by the cylinder 1, the plug 2, and the cover member 4. After kneading, the device can be used directly for filling kneaded cement into a target site or for applying the cement to a target site, thereby preventing entry of foreign matter or unwanted bacteria into the kneaded cement. Particularly, the O-rings 61 and 62 fitted to sliding surfaces of the plug 2 facilitate rotation of the shaft 31 and sliding of the plug 2 while maintaining closure of the device.

The stirring blades 321A can homogeneously knead the cement, irrespective of the viscosity of the cement. That is, the device can prepare kneaded cement of high viscosity, or low powder-liquid ratio, as well as kneaded cement of low viscosity, or high powder-liquid ratio. Kneaded cement of high viscosity features high formability and high strength. Kneaded cement of low viscosity can be filled into or applied to a target site by means of a fine injection needle.

Kneaded cements obtained by use of the kneading device were subjected to evaluation tests as follows.

Cement and a kneading liquid were kneaded in the proportions shown in Table 1 according to the method described above, thereby obtaining kneaded cements of Examples 1 and 2. The kneaded cement of Example 1 has a high viscosity and exhibits the consistency of clay. The kneaded cement of Example 2 has a low viscosity and can be extruded through an injection needle of gauge 18.

The kneaded cements of Comparative Examples 1 and 2 were obtained by kneading in a mortar the cement and the kneading liquid at powder-liquid ratio shown in Table 1.

TABLE 1

| | Cement | Kneading liquid | Powder-liquid weight ratio | Wet compressive strength |
|---|---|---|---|---|
| Example 1 | 20 g | 4.6 g | 0.23 | 598 kg/cm$^2$ |
| Example 2 | 20 g | 6.0 g | 0.30 | 465 kg/cm$^2$ |
| Comparative Example 1 | 20 g | 4.6 g | 0.23 | 613 kg/cm$^2$ |
| Comparative Example 2 | 20 g | 6.0 g | 0.30 | 421 kg/cm$^2$ |

Cement: equimolar powder mixture of calcium hydrogenphosphate and tetracalcium phosphate
Kneading liquid: pure water In order to examine the homogeneity of these kneaded cements, the kneading liquid contained a red pigment. The homogeneity of the kneaded cements was determined through visual observation for irregular color. The kneaded cements of Examples 1 and 2 exhibited a homogeneously kneaded state.

The kneaded cements of Examples 1 and 2 and of Comparative Examples 1 and 2 were tested for wet compressive strength according to the decay rate test method described in JIS T 6602. Specifically, each of the kneaded cements was filled into a die having a depth of 11 mm and a diameter of 6 mm and the cement was allowed to cure at a temperature of 37° C. and a relative humidity of 100% for 1 hour. The cured cement was then removed from the die and immersed in pseudo body fluid (aqueous solution containing $Na^+$ (142.0 mmol), $K^+$ (5.0 mmol), $Ca^{2+}$(2.5 mmol), $Mg^{2+}$ (1.5 mmol), $HCO_3^-$ (4.2 mmol), $Cl^-$ (148.0 mmol), $HPO_4^{2-}$ (1.0 mmol), $SO_4^{2-}$ (0.5 mmol), TRIS buffer (33.3 mmol), and hydrochloric acid (30 mM)) having a temperature of 37° C. for 24 hours. Subsequently, the cement was tested for wet compressive strength by use of a compressive strength test machine (product of Instron Corp.). The test results are shown in Table 1.

As seen from Table 1, the cements of Examples 1 and 2, which were prepared by means of the kneading device of the present invention, exhibit wet compressive strength values substantially equivalent to these exhibited by the kneaded cements of Comparative Examples 1 and 2, which were prepared by use of a mortar. That is, the method of the present invention yields kneaded cement in a kneading operation that is easier to carry out than that of the conventional method. The cement cures to a hardness equivalent to that associated with kneaded cement obtained by the conventional method.

Figure 10:
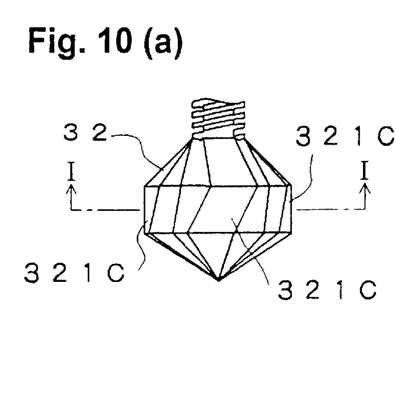
Figure 11:
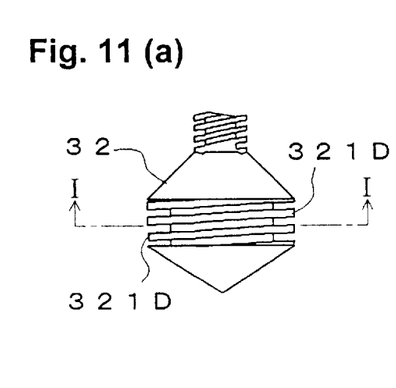
Figure 12:
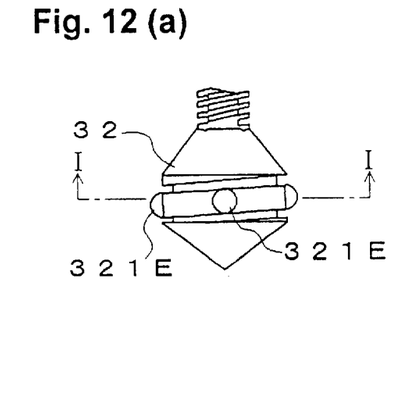

In order to examine the relationship between the form of the stirring blades 321 and the degree of mixing, kneading devices A, B, C, D and E were assembled having stirring blades 321A (FIG. 3), 321B (FIG. 9), 321C (FIG. 10), 321D (FIG. 11) and 321E (FIG. 12). These devices A, B, C, D and E were tested for kneading operability and the degree of mixing.

The device A having the stirring blades 321A shown in FIG. 3 produced good kneaded cement when the internal threads 21 and the shaft 31 had a thread pitch of about 10 mm. The time required for kneading was about 2 minutes. The percentage of residual kneaded cement after extrusion was not greater than 10%.

Figure 9:
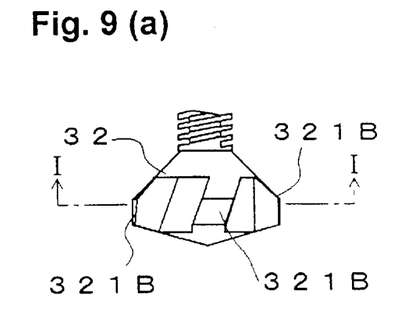

The device B having the stirring blades 321B shown in FIG. 9 produced good kneaded cement when the thread pitch was about 2.5 mm. Accordingly, the time required for kneading was longer than that required in the case of the stirring blade 321A. Similarly, the device C having the stirring blades 321C shown in FIG. 10 produced good kneaded cement.

The devices D and E having the stirring blades 321D and 321E of FIGS. 11 and 12, respectively, had the disadvantage that cement powder was caught in the gap between the stirring blades 321D and between the stirring blades 321E, resulting in a tendency toward lower homogeneity of kneaded cement as compared to the devices A, B, and C.

Figure 7:
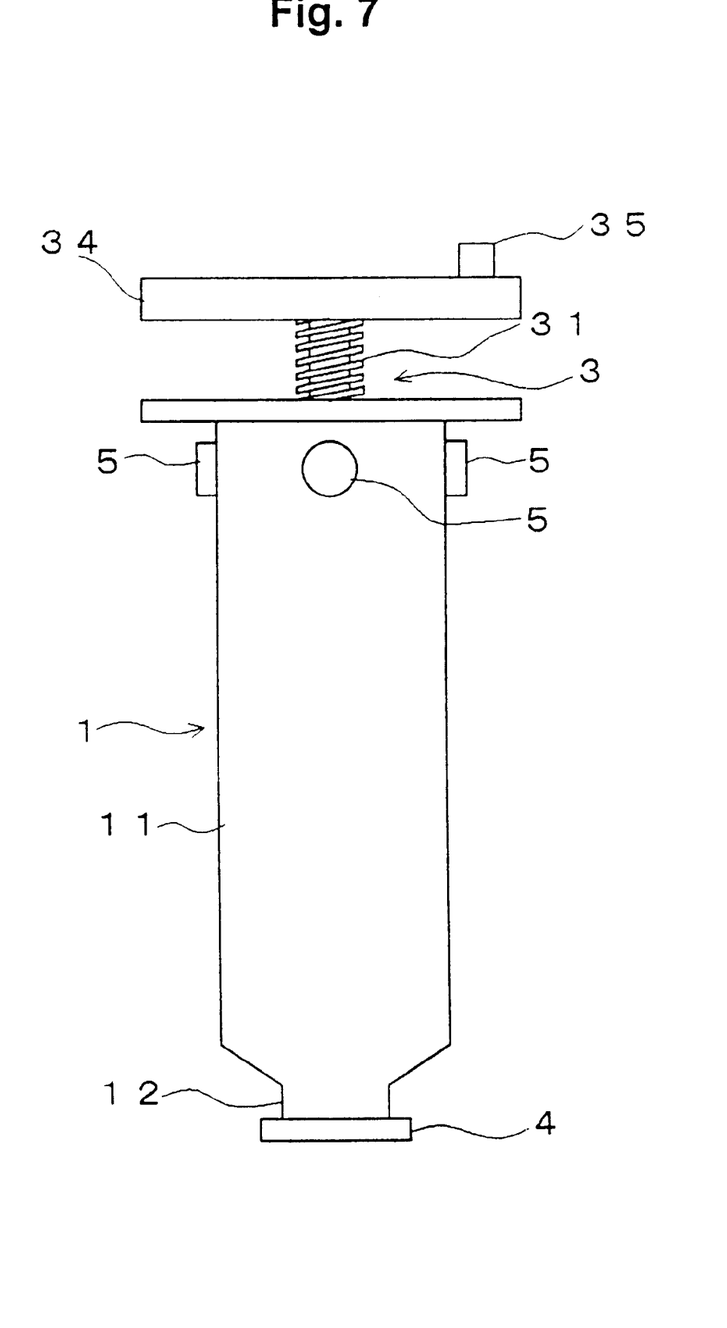
FIGS. 7 and 8 are, respectively, side and side sectional views of a second device according to the invention, incorporating alternative forms of kneading element.
Figure 8:
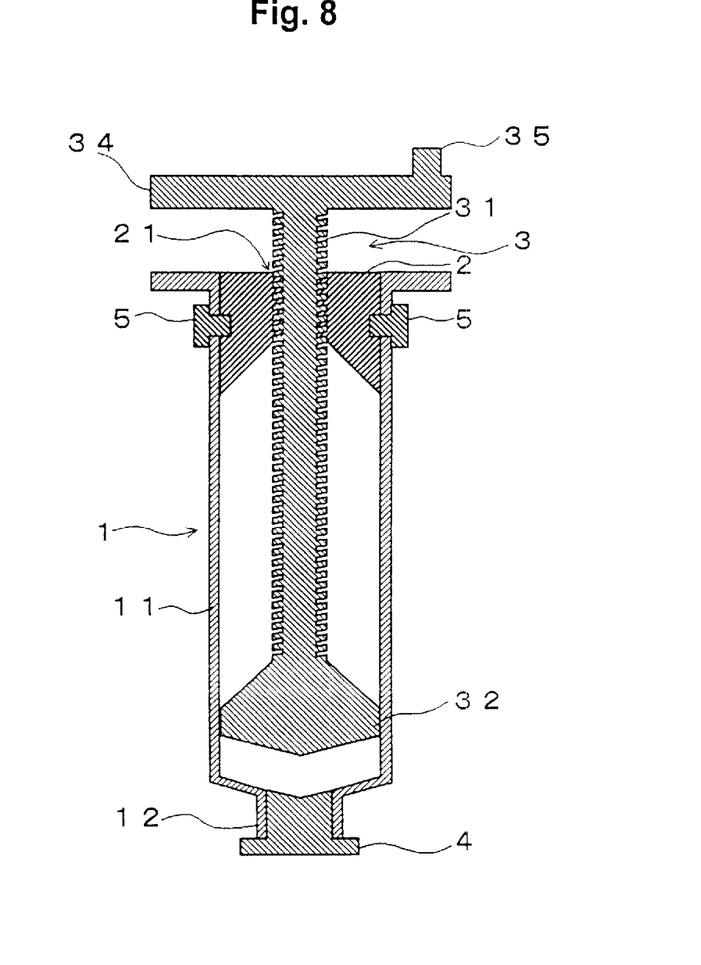

The present invention has been described with reference to specific embodiments, but may be embodied in many other specific forms according to objectives or applications without departing from the spirit or scope of the invention. For example, the cover member for the nozzle 12 may assume a plug-type form as shown in FIGS. 7 and 8. Alternatively, the cover member for the nozzle 12 may assume the form of a protrusion 4a as shown in FIG. 13(a), which is integrally formed with the cylinder 1 and can be broken off. A device having the protrusion 4a, which serves as a cover member for the nozzle, prevents escape of cement or kneaded cement from the cylinder through the nozzle unless the protrusion is broken off. Also, the device having the protrusion 4a permits immediate observation as to whether it has been used.

The form of the stirring blades can be modified according to the intended application. For example, the stirring blades may be arranged to incline with respect to the axis of the kneading element. Alternatively, the stirring blades may be arranged non-symmetrically with respect to the axis of the kneading element.

The above embodiments have been described using a pin-type stop member. However, the device is not limited thereto. The stop member may assume the form of other anchoring means without particular limitation. For example, as shown in FIG. 13(a), an upper portion of the cylinder 1 may be formed with an elastic portion 5a serving as a stop member. A protrusion 51a formed on the elastic portion 5a engages the plug 2 to thereby locate the plug in position. Alternatively, as shown in FIG. 13(b), a portion of the plug 2 may be formed into an elastic portion 5b serving as a stop member. A protrusion 51b formed on the elastic portion 5b is engaged by the cylinder 1 to thereby locate the plug in position. Since the elastic portions 5a and 5b are a portion of the cylinder 1 and the plug 2, respectively, such stop members cannot become lost or misplaced.

By use of the kneading device of the present invention and the method for preparing kneaded calcium phosphate-based cement using it, calcium phosphate-based cement can be quickly prepared through kneading and filled into or applied to a target site. Also, entry of foreign matter or unwanted bacteria into the device in the course of kneading can be prevented. Further, homogeneously kneaded cement can be obtained irrespective of the viscosity of the cement.

As a result of the kneading element including the stirring blades described above, kneading can be performed more homogeneously. Use of the O-rings facilitates the kneading operation, and entry of foreign matter or unwanted bacteria into the kneader in the course of kneading can be prevented more effectively.

While the invention has been described in detail and with reference to specific embodiments thereof, it will be apparent to one skilled in the art that various changes and modifications can be made therein without departing from the spirit and scope thereof.

This application is based on Japanese Patent Application No. Hei. 11-287302 filed Oct. 7, 1999 which is incorporated herein by reference in its entirety.

What is claimed is:

1. A kneading device adapted for preparing calcium phosphate-based cement, said device comprising: a cylinder, which includes a hollow cylindrical body portion and a nozzle formed at a distal end of said cylindrical body portion; a plug including an axial through-hole slidably disposed within a proximal end of said cylindrical body portion; a piston assembly which includes a shaft extending through said through-hole of said plug for axial and rotatable movement, a kneading element at the distal end of said shaft within said cylindrical body portion and a handle formed at the proximal end of said shaft portion; a cover member attached to and forming a closure for said nozzle and a stop member at the proximal end of said cylindrical body portion for fixing the plug within the cylinder at a predetermined position during a kneading operation.

2. The kneading device of claim 1, wherein said kneading element incorporates a stirring blade disposed along circumferentially peripheral edges thereof.

3. The kneading device of claim 1, wherein an outer surface of said plug has a groove formed therein, said device including an O-ring of an elastomeric material located within said groove thereby to form a seal between said outer surface of said plug and an interior of said hollow cylindrical body portion.

4. The kneading device of claim 1, wherein an inner surface of said plug as defined by said through-hole has a circumferential groove formed therein, said device further including an O-ring of an elastomeric material located within said groove thereby to form a seal between the plug shaft of said piston assembly and an inner surface of said plug.

5. The kneading device of claim 1, wherein said shaft has external threads, the plug has internal threads, and the external threads of the shaft engage the internal threads of the plug.

6. The kneading device of claim 5, wherein said thread has a pitch of 5–25 mm.

7. A method for preparing calcium phosphate-based cement, said method comprising the steps of:

providing a kneading device adopted for preparing calcium phosphate-based cement, said device comprising: a cylinder, which includes a hollow cylindrical body portion and a nozzle formed at a distal end of said cylindrical body portion; a plug including an axial through-hole slidably disposed within a proximal end of said cylindrical body portion; a piston assembly which includes a shaft extending through said through-hole of said plug for axial and rotatable movement, a kneading element at the distal end of said shaft within said cylindrical body portion and a handle formed at the proximal end of said shaft portion; a cover member attached to and forming a closure for said nozzle; and a stop member at the proximal end of said cylindrical body portion for fixing the plug within the cylinder at a predetermined position during a kneading operation;

introducing calcium phosphate-based cement and a kneading liquid into the space defined by the cylinder and the plug of the kneading device;

rotating and vertically moving the piston assembly within the cylinder so as to thereby knead the calcium phosphate-based cement and the kneading liquid into kneaded cement, moving the piston assembly such that the kneading element cement into contact with the plug, and detaching the cover member and the stop member; and moving the piston assembly and plug towards the nozzle so as thereby to extrude the kneaded cement from the cylinder through the nozzle.

* * * * *